US008509919B2

(12) United States Patent
Yoo et al.

(10) Patent No.: US 8,509,919 B2
(45) Date of Patent: Aug. 13, 2013

(54) SPATIALLY SELECTIVE VAGUS NERVE STIMULATION

(75) Inventors: Paul B. Yoo, Raleigh, NC (US); Warren M. Grill, Chapel Hill, NC (US); Juan Gabriel Hincapie Ordonez, Maple Grove, MN (US)

(73) Assignees: Cardiac Pacemakers, Inc., St. Paul, MN (US); Duke University, Durham, NC (US)

( * ) Notice: Subject to any disclaimer, the term of this patent is extended or adjusted under 35 U.S.C. 154(b) by 59 days.

(21) Appl. No.: 13/114,626

(22) Filed: May 24, 2011

(65) Prior Publication Data
US 2011/0301658 A1 Dec. 8, 2011

Related U.S. Application Data

(60) Provisional application No. 61/351,181, filed on Jun. 3, 2010.

(51) Int. Cl.
*A61N 1/18* (2006.01)
(52) U.S. Cl.
USPC .............................. 607/118; 607/48
(58) Field of Classification Search
USPC .................... 607/2, 42, 46, 48, 118
See application file for complete search history.

(56) References Cited

U.S. PATENT DOCUMENTS

| 5,700,282 | A | * | 12/1997 | Zabara | 607/9 |
|---|---|---|---|---|---|
| 6,104,956 | A | | 8/2000 | Naritoku et al. | |
| 6,466,822 | B1 | | 10/2002 | Pless | |
| 6,556,868 | B2 | | 4/2003 | Naritoku et al. | |
| 7,672,728 | B2 | * | 3/2010 | Libbus et al. | 607/42 |
| 8,233,982 | B2 | * | 7/2012 | Libbus | 607/14 |
| 2002/0072776 | A1 | | 6/2002 | Osorio et al. | |
| 2005/0137645 | A1 | | 6/2005 | Voipio et al. | |
| 2006/0282127 | A1 | | 12/2006 | Zealear | |
| 2008/0058873 | A1 | | 3/2008 | Lee et al. | |
| 2008/0058874 | A1 | * | 3/2008 | Westlund et al. | 607/2 |
| 2008/0058892 | A1 | | 3/2008 | Haefner et al. | |
| 2009/0228078 | A1 | * | 9/2009 | Zhang et al. | 607/62 |
| 2010/0010556 | A1 | | 1/2010 | Zhao et al. | |

FOREIGN PATENT DOCUMENTS

| WO | WO-03100933 A1 | 5/2003 |
|---|---|---|
| WO | WO-2010031406 A1 | 3/2010 |
| WO | WO-2010051499 A1 | 5/2010 |
| WO | WO-2011153024 A1 | 12/2011 |

OTHER PUBLICATIONS

"International Application Serial No. PCT/US2011/037726, Int'l Search Report mailed Nov. 17, 2011", 5 pags.

(Continued)

*Primary Examiner* — Brian T Gedeon
(74) *Attorney, Agent, or Firm* — Schwegman Lundberg & Woessner, P.A.

(57) ABSTRACT

By targeting on selected branches or fascicles of a vagus nerve using electrode placement and/or selection, one or more target branches of the vagus nerve are substantially activated by electrical stimulation pulses delivered to a branch without substantially activating one or more non-target branches. In one embodiment, vagus nerve stimulation is delivered through an electrode placed on a thoracic vagus nerve that is separated from a recurrent laryngeal nerve, such that the vagus nerve is stimulated without causing laryngeal muscle contractions. In another embodiment, vagus nerve stimulation is delivered through a multi-contact electrode with one or more contacts selected for delivering the electrical stimulation pulses to stimulate the vagus nerve without causing laryngeal muscle contractions.

20 Claims, 6 Drawing Sheets

(56) References Cited

OTHER PUBLICATIONS

"International Application Serial No. PCT/US2011/037726, Written Opinion mailed Nov. 17, 2011", 7 pgs.

"International Application Serial No. PCT/US2011/037726, International Preliminary Report on Patentability mailed Dec. 13, 2012", 9 pgs.

* cited by examiner

SPATIALLY SELECTIVE VAGUS NERVE STIMULATION

CLAIM OF PRIORITY

This application claims the benefit of priority under 35 U.S.C. §119(e) of U.S. Provisional Patent Application Ser. No. 61/351,181, filed on Jun. 3, 2010, which is herein incorporated by reference in its entirety.

TECHNICAL FIELD

This document relates generally to neurostimulation and more particularly to spatially selective vagus nerve stimulation for substantially activating one or more target nerve branches without substantially activating one or more non-target nerve branches.

BACKGROUND

Vagus nerve stimulation (VNS) has been applied to modulate various physiologic functions and treat various diseases. One example is the modulation of cardiac functions in a patient suffering heart failure or myocardial infarction. The myocardium is innervated with sympathetic and parasympathetic nerves including the cardiac branches of the vagus nerve. Activities in the vagus nerve, including artificially applied electrical stimuli, modulate the heart rate and contractility (strength of the myocardial contractions). Electrical stimulation applied to the vagus nerve is known to decrease the heart rate and the contractility, lengthening the systolic phase of a cardiac cycle, and shortening the diastolic phase of the cardiac cycle. This ability of VNS is utilized, for example, to control myocardial remodeling.

In addition to treating cardiac disorders such as myocardial remodeling, VNS is also known to be effective in treating disorders including, but not limited to, depression, anorexia nervosa/eating disorders, pancreatic function, epilepsy, hypertension, inflammatory disease, and diabetes. Because many physiological functions are controlled or affected by the neural activities in the vagus nerve, there is a need to control VNS for the desirable functional outcome while minimizing side effects.

SUMMARY

By targeting on selected branches or fascicles of a vagus nerve using electrode placement and/or selection, delivery of electrical stimulation pulses is controlled to substantially activate one or more target branches of the vagus nerve without substantially activating one or more non-target branches.

In one embodiment, electrical stimulation pulses are delivered to an electrode placed on or adjacent to a first branch of the vagus nerve. The first branch is separate from a second branch of the vagus nerve and selected to allow for substantial activation of one or more target branches of the vagus nerve by the electrical stimulation pulses without substantially activating the second branch.

In one embodiment, electrical stimulation pulses are delivered to an electrode placed on a portion of a cervical vagus nerve trunk or a portion of a thoracic vagus nerve (tVN). The delivery of the electrical stimulation pulses is controlled such that one or more target branches of the vagus nerve are activated by the electrical stimulation pulses without causing contraction of a laryngeal muscle innervated by a recurrent laryngeal nerve (RLN).

In one embodiment, a system for stimulating the vagus nerve includes an electrode, a neural sensing circuit, a myoelectric sensing circuit, and a neurostimulator. The electrode is placed on a first branch of the vagus nerve to allow for delivery of electrical stimulation pulses to the first branch. The neural sensing circuit senses a stimulation-evoked electroneurographic (ENG) signal representative of a response of the vagus nerve to the electrical stimulation pulses. The myoelectric sensing circuit senses a stimulation-evoked electromyographic (EMG) signal representative of a response of a muscle to the electrical stimulation pulses, the muscle innervated by a second branch of the vagus nerve. The neurostimulator includes a stimulation circuit and a stimulation control circuit. The stimulation circuit delivers the electrical stimulation pulses to the first branch through the electrode. The stimulation control circuit controls the delivery of the electrical stimulation pulses using a plurality of stimulation parameters and includes a parameter adjuster that allows for adjustment of one or more stimulation parameters of the plurality of stimulation parameters using the ENG signal and the EMG signal.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

Figure 1:
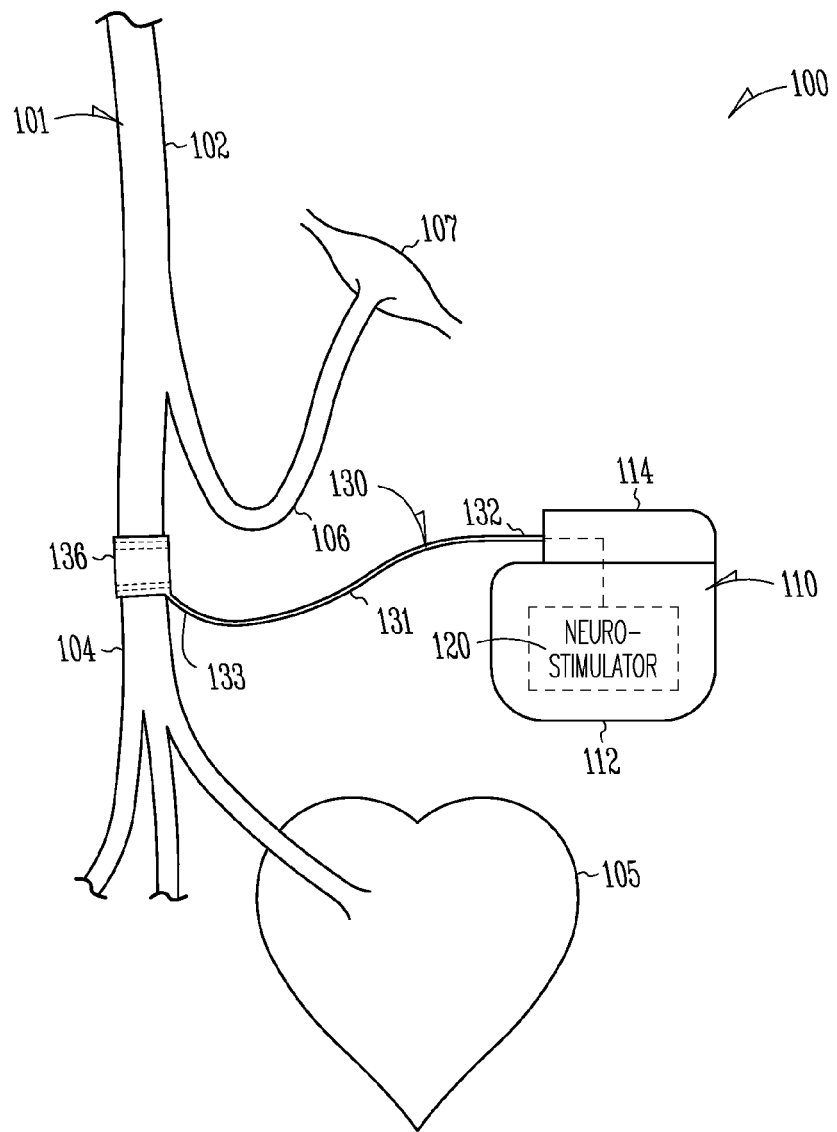
FIG. 1 is an illustration of an embodiment of a vagus nerve stimulation (VNS) system and portions of an environment in which the VNS system is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a method and system for stimulating the vagus nerve to modulate one or more target functions while minimizing stimulation-evoked side effects. Vagus nerve stimulation (VNS) has been used for the treatment of neurological disorders including depression and epilepsy. VNS is also investigated for treatment of various disorders such as Alzheimer's disease, anxiety, heart failure, and obesity.

The vagus nerve originates in the medulla and targets multiple organs in a person's body through a complex functional innervation pattern. There are both efferent and afferent nerve fibers within the vagus nerve trunk that convey neural activities to and from visceral organs such as the esophagus, gastrointestinal tract, kidney and pancreas (abdominal branch of vagus), thoracic organs such as the heart and lungs (thoracic branch of vagus), and voluntary muscles of the neck and multiple segments of the upper airway (recurrent laryngeal nerve, RLN). Such complexity has been significantly limiting the effectiveness of VNS and the overall patient population that may benefit from this therapy.

The difficulty in therapeutic application of VNS is further complicated by the total number of fibers within the vagus nerve trunk and the distribution of nerve fibers having different diameter. In an adult dog, which has been used as an animal model for the human vagus nerve, the cervical vagus nerve trunk contains approximately 20,000 myelinated neurons and an even greater number of unmyelinated neurons. Both the human and canine vagus nerves also share a common classification scheme defined by the diameter of nerve fibers. This is based on the classical designation of A (myelinated), B (myelinated parasympathetic) and C (unmyelinated) type fibers, as summarized in Table 1.

TABLE 1

Summary of Vagus Nerve Fiber Type Properties.

| | A-Fibers | B-Fibers | C-Fibers |
|---|---|---|---|
| Diameter (μm) | 5-20 | 1-3 | 0.2-2 |
| Myelinated | Yes | Yes | No |
| Conduction Velocity (m/s) | 30-120 | 3-20 | 0.3-2 |
| Per-Unit Latencies (ms/cm) | 0.08-0.3 | 0.5-3.3 | 5-33.3 |

Currently, a typical site of electrode implantation for VNS therapy is at the cervical spinal level between the thyroid cartilage and the sternum of the patient. At this location, the vagus nerve contains a wide array of nerve fibers, as summarized in Table 1. As a result, stimulation parameters used for VNS therapy are largely determined by titrating the various temporal properties of the electrical pulses (e.g., amplitude, frequency, duty cycle). Various studies applying VNS to animal models and human patients led to the establishment of recommended clinical parameters for antiepileptic and other applications of VNS. However, stimulation-evoked side effects, such as voice hoarseness, coughing, and pain, remain a problem in applying VNS therapy. These unwanted effects of VNS result from (1) the reversed recruitment order of myelinated nerve fibers during electrical stimulation (i.e., lower activation threshold for larger diameter fibers) and (2) the vast majority of larger diameter fibers within the vagus nerve innervate the voice box and upper airway via the RLN. Delivering electrical stimulation to the vagus nerve through bipolar helical nerve cuff electrode, for example, is known to result in non-selective activation of all nerve fibers within the nerve trunk, and hence little control over unintended generation of side-effects including unintended laryngeal activities.

The present method and system provide for spatially selective activation of vagus nerve branches to maximize overall therapeutic efficacy of VNS. In this document, "spatially selective activation of vagus nerve branches" refers to activation of one or more selected (or specified) vagus nerve branches by delivering electrical stimulation to a space, such as a particular segment or branch of the vagus nerve, identified to allow for activation of the one or more selected vagus nerve branches without causing an unwanted side effect such as activated of a non-selected vagus nerve branch. By targeting on selected branches or fascicles of the vagus nerve using electrode placement and/or selection, the electrical stimulation is delivered to activate one or more target nerve pathways while minimizing activation of one or more non-target nerve pathways associated with stimulation-evoked side effects. In one embodiment, VNS is delivered to a thoracic vagus nerve (tVN) in a location separate from the RLN to allow placement of an electrode on the tVN but isolated from the RLN, such that the delivery of the electrical stimulation through this electrode results in desirable modulation of cardiovascular functions without evoking unwanted laryngeal activities. Surgical separation of a portion of the tVN from the RLN may be required to create adequate space for such electrode placement. In another embodiment, the topographical organization of the nerve fascicles of the cervical vagus nerve trunk allows target selection using a single multi-contact nerve electrode. The contacts in the nerve electrode are selected for delivering VNS to result in the desirable modulation of cardiovascular functions without evoking the unwanted side effects caused by activation of one or more non-targeted fibers of the vagus nerve. While efferent laryngeal muscle contraction is discussed as a specific example of the unwanted side effects to be avoided using the present method and system, the present subject matter applies to control of unwanted side effects by spatially selective activation of vagus nerve branches. Another example of such unwanted side effects to be avoided using the present method and system includes airway reflexes evoked by (1) direct activation of afferent RLN fibers and/or (2) indirect activation of afferent RLN activity generated by efferent laryngeal muscle contractions.

FIG. 1 is an illustration of an embodiment of a VNS system 100 and portions of an environment in which system 100 is used. FIG. 1 shows a portion of a vagus nerve 101 having segments or branches including a cervical vagus nerve trunk 102, a tVN 104, and an RLN 106. In the illustrated embodiment, the physical separation between tVN 104 and RLN 106 after they diverge from cervical vagus nerve trunk 102 allows placement of a stimulation electrode 136 on tVN 104. Electrode 136 allows for delivery of VNS to tVN 104, which innervates thoracic organs, including a heart 105, and abdominal organs through further branches of the vagus nerve, without activating the RLN, which innervates laryngeal muscles (represented in FIG. 1 by a laryngeal muscle 107). The physical separation between tVN 104 and RLN 106 may be created or partially created by surgery to allow for proper placement of electrode 136 without affecting neural conduction within these nerve branches. In one embodiment, tVN 104 and RLN 106 are longitudinally separated by dissecting the portion of the vagus nerve trunk including these two branches to the location where fibers of tVN 104 and RLN 106 diverge, at approximately the level of the subclavian artery. In one embodiment, electrode 136 is placed on tVN 104 within about one centimeter from the location where tVN 104 and RLN 106 diverge.

While the application involving tVN 104 and RLN 106 as illustrated in FIG. 1 is discussed as a specific example in this document, the present method may apply to other branches of the vagus nerve or other nerves being targets of neurostimulation. In various embodiments, a portion of a nerve trunk such as a vagus nerve trunk including a first branch and a second branch is dissected to separate the first and second branches. The first branch controls one or more physiological functions of a patient. The second branch controls one or more other physiological functions of the patient. The first branch includes the stimulation site to which the electrical stimulation is delivered. The second branch is a non-target branch that is not intended to be activated by the electrical stimulation pulses. The one or more target branches, which include but are not limited to the first branch, are intended to be activated by the electrical stimulation. The stimulation electrode is placed on the first branch to allow for delivery of electrical stimulation to activate one or more target branches of the nerve trunk (including the first branch) without activating the second branch.

In the illustrated embodiment, system 100 includes an implantable medical device 110 electrically coupled to electrode 136 through an implantable lead 130. Implantable medical device 110 includes a neurostimulator 120 encapsulated by an implantable housing 112, and a header 114 attached to implantable housing 112 and providing for connection to lead 130. Neurostimulator 120 is discussed below with reference to FIG. 2. In one embodiment, implantable medical device 110 is a neurostimulator. In other embodiments, in addition to neurostimulator 120, implantable medical device 110 includes one or more of a cardiac pacemaker, a cardioverter/defibrillator, a drug delivery device, a biologic therapy device, and any other monitoring or therapeutic devices. In the illustrated embodiment, lead 130 includes a proximal end 132, a distal end 133, and an elongate body 131 coupled between proximal end 132 and distal end 133. Proximal end 132 is configured to be connected to implantable medical device 110. Distal end 133 includes, or is otherwise coupled to, electrode 136. Electrode 136 is a bipolar nerve cuff electrode. In another embodiment, electrode 136 is a monopolar nerve cuff electrode, and another electrode such as a portion of implantable housing 112 is used. In various embodiments, electrode 136 includes any form of electrode that allows for activation of tVN 104 by electrical stimulation delivered from neurostimulator 120.

While FIG. 1 illustrates the embodiment in which the placement of electrode 136 on tVN 104 allows for VNS to modulate cardiovascular functions without evoking unwanted laryngeal activities, the present subject matter generally includes selective activation of vagus nerve branches by selecting the sites to which the electrical stimulation pulses are delivered through multiple electrodes or a multi-contact electrode. For example, a multi-contact electrode may be placed in cervical vagus nerve trunk 102, cranial to the location where tVN 104 and RLN 106 diverge. Stimulation is delivered through various combination of contacts of the multi-contact electrode to select one or more contacts allowing for the VNS to substantially activate tVN 104 without substantially activating RLN 106.

Figure 2:
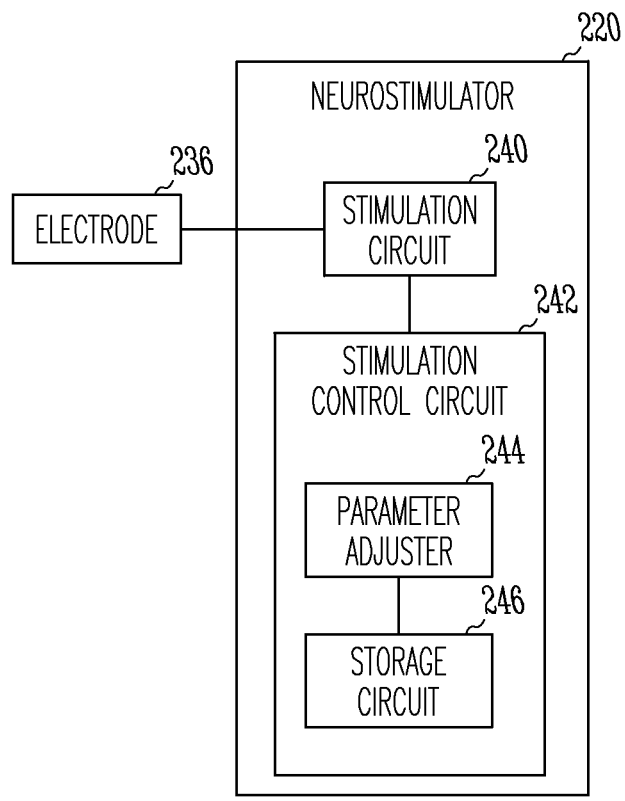
FIG. 2 is a block diagram illustrating an embodiment of an electrode and a neurostimulator of the VNS system.

FIG. 2 is a block diagram illustrating an embodiment of an electrode 236 and a neurostimulator 220. Electrode 236 represents an embodiment of electrode 136. Neurostimulator 220 represents an embodiment of neurostimulator 120.

Neurostimulator 220 includes a stimulation circuit 240 and a stimulation control circuit 242. Stimulation circuit 240 produces electrical stimulation pulses and delivers the electrical stimulation pulses to electrode 236. Stimulation control circuit 242 controls the delivery of the electrical stimulation pulses using a plurality of stimulation parameters and includes a parameter adjuster 244 and a storage circuit 246. Parameter adjuster 244 allows for adjustment of one or more stimulation parameters of the plurality of stimulation parameters such that the intensity of the electrical stimulation pulses is provided for substantially activating one or more target branches of a nerve such as the vagus nerve without substantially activating one or more non-target branches of the nerve. In one embodiment, the plurality of stimulation parameters includes pulse amplitude, pulse width, pulse frequency, duty cycle, cycle unit, and stimulation duration. The pulse amplitude is the amplitude of each electrical stimulation pulse specified as voltage (e.g., for constant-voltage pulse) or current (e.g., for constant-current pulse). The pulse width is the duration of each electrical stimulation pulse. The pulse frequency is the frequency at which the electrical stimulation pulses are delivered and may also be specified as an inter-pulse interval being the time interval between successive pulses. The duty cycle is the ratio of a stimulation interval to the cycle unit. The electrical stimulation pulses are delivered during only the stimulation interval. The stimulation duration is the duration of a delivery of neurostimulation therapy. The cycle unit and the stimulation durations may be specified by time or number of pulses, and the duty cycles may be specified by time or number of pulses in each cycle unit. For example, "pulses delivered at a pulse frequency of 20 Hz at a duty cycle of 10% and a unit cycle of 1 second" is equivalent to "pulses delivered at a pulse frequency of 20 Hz at a duty cycle of 2 pulses per unit cycle of 20 pulses".

Storage circuit 246 stores values for the plurality of stimulation parameters. In one embodiment, storage circuit 246 stores values of the one or more stimulation parameters selected to substantially activate the one or more target branches of the nerve without substantially activating the one or more non-target branches of the nerve. In one embodiment, a value of the pulse amplitude is selected to substantially activate the one or more target branches of the nerve without substantially activating the one or more non-target branches of the nerve, and stored in storage circuit 246.

In various embodiments, the circuit of neurostimulator 220, including its various elements discussed in this document, is implemented using a combination of hardware and software. In various embodiments, stimulation control circuit 242 may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 3:
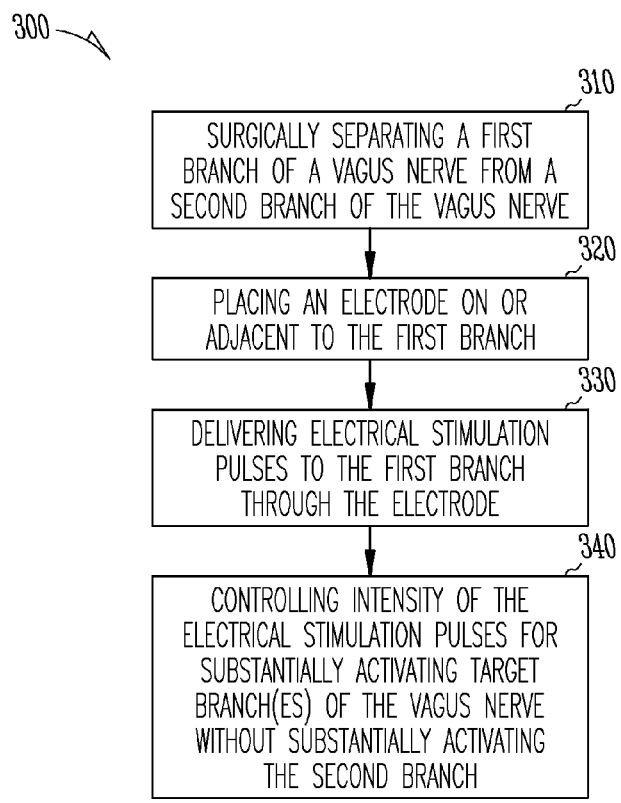
FIG. 3 is a flow chart illustrating an embodiment of a method of spatially selective VNS.

FIG. 3 is a flow chart illustrating an embodiment of a method 300 of spatially selective VNS. In one embodiment, method 300 is performed using system 100 including its embodiments discussed in this document.

At 310, if necessary for electrode placement, a portion of the vagus nerve including a first branch and a second branch is longitudinally dissected and separated, without damaging the normal neural conduction in these branches. At 320, an electrode, such as a nerve cuff electrode, is placed on or adjacent to the first branch.

At 330, electrical stimulation pulses are delivered to the first branch through the electrode placed on the first branch.

At 340, the delivery of the electrical stimulation pulses is controlled to substantially activate one or more target branches of the vagus nerve, including the first branch, without substantially activating the second branch. This includes adjusting one or more stimulation parameters controlling the intensity of the electrical stimulation pulses. In one embodiment, the one or more stimulation parameters are determined by monitoring neural signals and/or myoelectric signals indicative of the activation of the one or more target branches and the second branch. Surgical separation at 310 is not necessary if the electrode can be placed on or adjacent to the first branch to allow substantial activation of the one or more target branches of the vagus nerve, including the first branch, without substantially activating the second branch. In this document, substantially activating a nerve means causing a detectable stimulation-evoked neural response. Such stimulation-evoked neural response may be detected, for example, by sensing neural traffic in the nerve and/or sensing a signal indicative of a physiological function modulated by the neural traffic.

Figure 4:
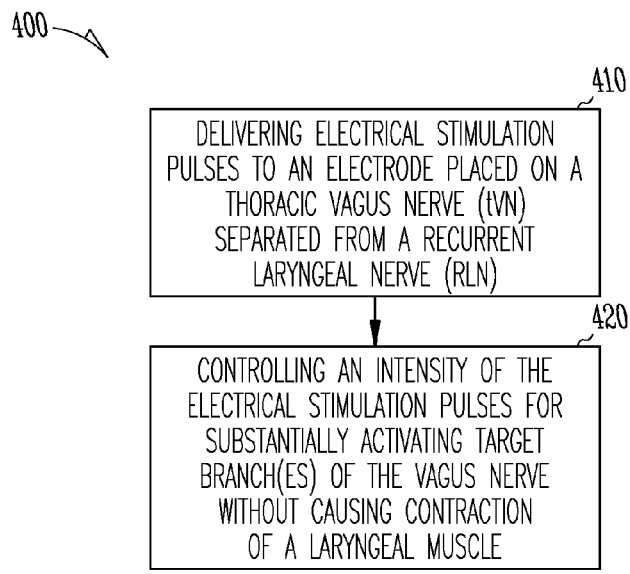
FIG. 4 is a flow chart illustrating another embodiment of a method of spatially selective VNS.

FIG. 4 is a flow chart illustrating an embodiment of a method 400 of spatially selective VNS. Method 400 includes an embodiment of method 300 with the first branch of the vagus nerve being tVN 104 and the second branch of the vagus nerve being RLN 106. In one embodiment, method 400 is performed using system 100 including its embodiments discussed in this document.

At 410, electrical stimulation pulses are delivered to tVN 104, which has been longitudinally separated from RLN 106. At 420, the intensity of the electrical stimulation pulses is controlled for substantially activating one or more target branches of the vagus nerve without causing contraction of a laryngeal muscle that is innervated by RLN 106.

In one embodiment, this intensity is determined by sensing signals representative and/or indicative of the neural responses to the delivery of the stimulation pulses. For example, a stimulation-evoked electroneurographic (ENG) signal representative of a response of the cervical vagus nerve trunk to the electrical stimulation pulses is sensed, and a stimulation-evoked electromyographic (EMG) indicative of the response of the RLN to the electrical stimulation pulses is sensed. The one or more target branches of the vagus nerve are considered to be substantially activated when the amplitude of the ENG signal exceeds a specified ENG threshold. The contraction of a laryngeal muscle is not considered to be occurring, or the RLN is not considered to be activated, when the amplitude of the EMG signal does not exceed a specified EMG threshold. In one embodiment, the intensity of the electrical stimulation pulses is determined by adjusting the pulse amplitude and/or the pulse width and observing the effect of the adjustment on the amplitude of the ENG signal and the amplitude of the EMG signal.

Figure 5:
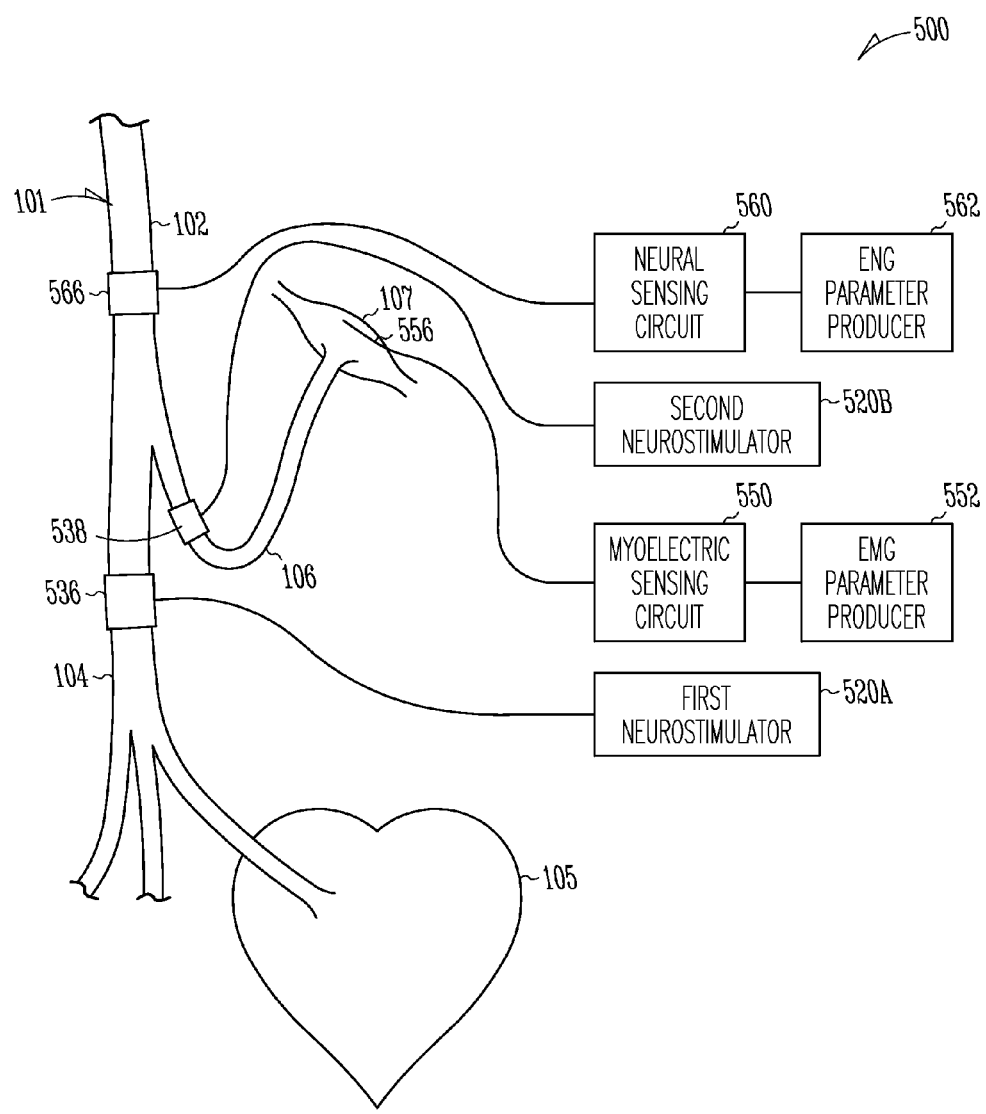
FIG. 5 is an illustration of a system for testing the method of FIG. 4.

FIG. 5 is an illustration of a system 500 for testing method 400. The vagus nerve 101 is dissected distally to approximately the level of the subclavian artery where multiple branches of the vagus nerve trunk can be separated and identified. RLN 106 and the remaining part of the vagus nerve (tVN 104) are isolated and instrumented with individual nerve cuff electrodes 538 (on or adjacent to RLN 106) and 536 (on or adjacent to tVN 104). A tripolar nerve cuff electrode 566 is implanted on cervical vagus nerve trunk 102 to record antidromic ENG activity, and an electrode 556 including a pair of insulated stainless steel wires was inserted into laryngeal muscle 107 (e.g., the posterior cricoarytenoid muscle) to measure laryngeal EMG.

A first neurostimulator 520A is electrically connected to electrode 536 to deliver electrical stimulation pulses to tVN 104. A second neurostimulator 520B is electrically connected to electrode 538 to deliver electrical stimulation pulses to RLN 106. An example for each of first neurostimulator 520A and second neurostimulator 520B is neurostimulator 220 as discussed above. For the purpose of the test, first neurostimulator 520A and second neurostimulator 520B may include one device being used as first neurostimulator 520A and second neurostimulator 520B at different times, or two devices that can be used concurrently or at different times. First neurostimulator 520A and second neurostimulator 520B may each be an implantable device or an external device that is electrically coupled to the corresponding electrode via an implantable or percutaneous lead. A neural sensing circuit 560 is electrically coupled to electrode 566 and senses a stimulation-evoked ENG signal representative of a response of cervical vagus nerve trunk 102 to the electrical stimulation pulses delivered to tVN 104 and the electrical stimulation pulses delivered to RLN 106. An ENG parameter producer 562 produces an amplitude of the ENG signal indicative of the response of cervical vagus nerve trunk 102 using the sensed ENG signal. A myoelectric sensing circuit 550 is electrically coupled to electrode 556 and senses a stimulation-evoked EMG signal indicative of the response to the electrical stimulation pulses delivered to tVN 104 and the electrical stimulation pulses delivered to RLN 106. An EMG parameter producer 552 produces an amplitude of the EMG signal indicative of the response of the laryngeal muscle using the sensed EMG signal.

Figure 6A:
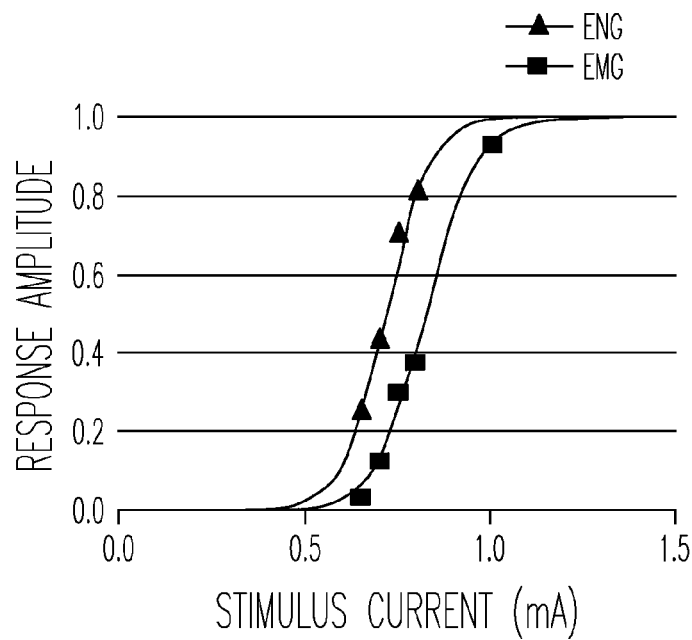
FIGS. 6A and 6B are illustrations of results of testing the method of FIG. 4.
Figure 6B:
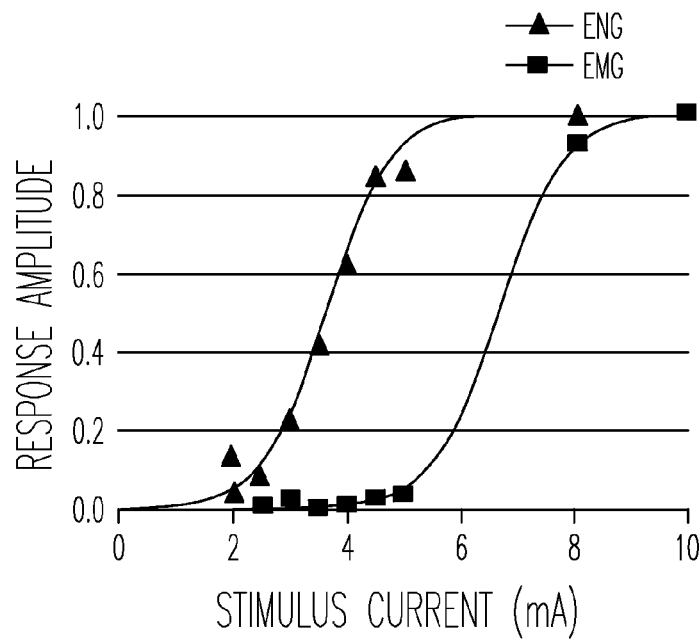

FIGS. 6A and 6B are illustrations of results of testing method 400. The feasibility of selectively activating individual branches of the vagus nerve was investigated using a canine model and system 500. FIGS. 6A and 6B show recruitment curves obtained by recording the stimulation-evoked ENG and EMG activities, which demonstrates a clear separation of nerves innervating the larynx from those of the vagus nerve that continued distally into the thorax. FIG. 6A shows that during selective RLN stimulation (through electrode 538), the concomitant activation of low-threshold A-fibers (current=0.5 mA) and laryngeal EMG activity indicates a strong correlation between these large diameter fibers and muscles of the larynx. In contrast, FIG. 6B shows that selective stimulation of the tVN (through electrode 536, for which a monopolar nerve cuff electrode was used) has a significantly higher threshold for activating ENG activity (current=2 mA), which reaches a plateau at approximately 4 mA. The activation of laryngeal EMG activity above 4 mA indicates that the threshold at which the tVN stimulation current spills over into the adjacent RLN branch, thus indicating a need to adjust stimulation intensity.

These results show that the anatomical divergence of multiple branches of the vagus nerve allows for selectively stimulating specific subsets of nerves within the vagus nerve to achieve desirable therapeutic effects while minimizing side-effects. The topographical organization of the nerve fascicles also allows for use of a single multi-contact nerve electrode as the neural interface for an implanted device.

In various embodiments, spatially selective VNS is applied by selecting a stimulation site on a specific nerve branch and a stimulation intensity to substantially activate the one or more target branches of the vagus nerve without substantially activating one or more non-target branches of the vagus nerve. A nerve is substantially activated when the stimulation-evoked neural response is detectable (such as when the amplitude of an ENG signal is at or above a specified ENG threshold) or when a stimulation-evoked response being a physiological function controlled by the nerve is detectable (such as when the amplitude of the EMG signal is at or above a specified EMG threshold). Likewise, a nerve is not substantially activated when the stimulation-evoked neural response is not detectable (such as when the amplitude of an ENG signal is below a specified ENG threshold) or when a stimulation-evoked response being a physiological function controlled by the nerve is detectable (such as when the amplitude of the EMG signal is below a specified EMG threshold).

Figure 7:
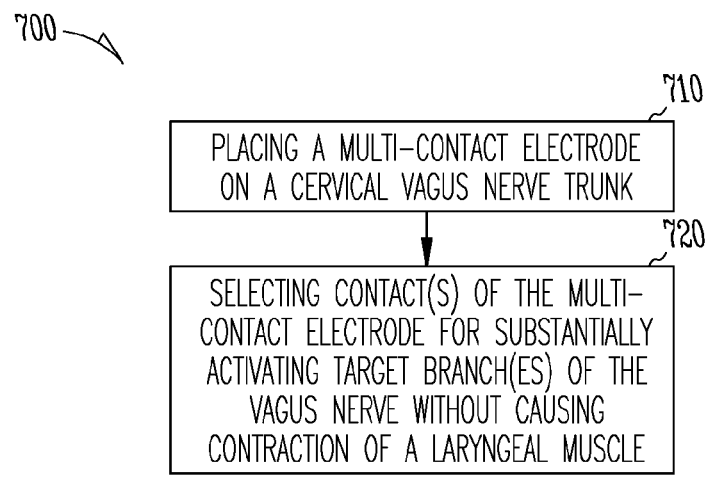
FIG. 7 is a flow chart illustrating an embodiment of another method of spatially selective VNS.

FIG. 7 is a flow chart illustrating an embodiment of a method 700 of spatially selective VNS. In one embodiment, method 700 is performed using system 100 including its embodiments discussed in this document, with electrode 136 being a multi-contact electrode.

At 710, a multi-contact electrode is placed on cervical vagus nerve trunk 102 cranial to the location where tVN 104 and RLN 106 diverge. The contacts of the multi-contact electrode are distributed to allow selective stimulation of the fascicles of cervical vagus nerve trunk 102. At 720, one or more contacts of the multi-contact electrode are selected for substantially activating one or more target branches of the vagus nerve without causing contraction of a laryngeal muscle that is innervated by RLN 106. Electrical stimulation pulses are delivered through various contacts or combination of contacts to identify the one or more contacts to be selected. Stimulation control circuit 242 controls the delivery of the electrical stimulation pulses using the plurality of stimulation parameters including one or more stimulation parameters specifying the selection of the one or more contacts of the multi-contact electrode. Parameter adjuster 244 adjusts the one or more stimulation parameters during the process of selecting the one or more contacts. The one or more stimulation parameters specifying the one or more contact selected at completion of this process are stored in storage circuit 246 for the subsequent VNS therapy.

In one embodiment, the electrical stimulation pulses are delivered using at least two contacts of the multi-contact electrode used as a bipolar electrode. In another embodiment, the electrical stimulation pulses are delivered using at least one contact of the multi-contact electrode used as a monopolar electrode and a separate electrode.

In one embodiment, this process of selecting the one or more contacts includes sensing signals representative and/or indicative of the neural responses to the delivery of the stimulation pulses. For example, a stimulation-evoked electroneurographic (ENG) signal representative of a response of the cervical vagus nerve trunk to the electrical stimulation pulses is sensed, and a stimulation-evoked electromyographic (EMG) indicative of the response of the RLN to the electrical stimulation pulses is sensed. The one or more target branches of the vagus nerve are considered to be substantially activated when the amplitude of the ENG signal exceeds a specified ENG threshold. The contraction of a laryngeal muscle is not considered to be occurring, or the RLN is not considered to be activated, when the amplitude of the EMG signal does not exceed a specified EMG threshold. In one embodiment, the process of selecting the one or more contacts includes sweeping through various contacts and/or combination of contacts of the multi-contact electrode and observing the effect of the adjustment on the amplitude of the ENG signal and the amplitude of the EMG signal.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A method for electrically stimulating a vagus nerve in a living body, the method comprising:
   delivering electrical stimulation pulses to an electrode placed on or adjacent to a portion of a first branch of the vagus nerve, the portion of the first branch surgically separated from a second branch of the vagus nerve and selected to allow for substantial activation of one or more target branches of the vagus nerve by the electrical stimulation pulses without substantially activating the second branch, wherein the electrode is isolated from the second branch.

2. The method of claim 1, wherein delivering the electrical stimulation pulses to the electrode comprises delivering the electrical stimulation pulses from an implantable medical device through an implantable lead coupled to the implantable medical device and including or coupled to the electrode.

3. The method of claim 2, wherein delivering the electrical stimulation pulses to the electrode comprises delivering the electrical stimulation pulses to a cuff electrode.

4. The method of claim 1, wherein the first branch is a thoracic vagus nerve (tVN), and the second branch is a recurrent laryngeal nerve (RLN).

5. The method of claim 4, comprising controlling one or more cardiovascular functions by adjusting one or more stimulation parameters controlling the activation of the one or more target branches of the vagus nerve by the electrical stimulation pulses.

6. The method of claim 4, comprising:
   sensing a stimulation-evoked electroneurographic (ENG) signal representative of a response of the one or more target branches to the electrical stimulation pulses;
   sensing a stimulation-evoked electromyographic (EMG) signal representative of a response of a laryngeal muscle to the electrical stimulation pulses; and
   controlling an intensity of the electrical stimulation pulses using an amplitude of the ENG signal and an amplitude of the EMG signal.

7. The method of claim 1, wherein delivering the electrical stimulation pulses to the electrode placed on or adjacent to the portion of the first branch of the vagus nerve comprises delivering the electrical stimulation pulses to the electrode placed on a portion of a cervical vagus nerve trunk or a portion of a thoracic vagus nerve (tVN), and further comprising controlling the delivery of the electrical stimulation pulses such that one or more target branches of the vagus nerve are activated by the electrical stimulation pulses without causing contraction of a laryngeal muscle innervated by a recurrent laryngeal nerve (RLN).

8. The method of claim 7, comprising:
   delivering the electrical stimulation pulses to the electrode placed on the portion of the tVN; and
   controlling an intensity of the electrical stimulation pulses such that the one or more target branches of the vagus nerve are activated by the electrical stimulation pulses without causing the contraction of the laryngeal muscle innervated by the RLN.

9. The method of claim 8, wherein controlling the intensity of the electrical stimulation pulses comprises adjusting a pulse amplitude of the electrical stimulation pulses.

10. The method of claim 7, comprising:
    delivering the electrical stimulation pulses to a multi-contact electrode placed on the portion of the cervical vagus nerve trunk; and
    selecting one or more contacts of the multi-contact electrode for delivering the electrical stimulation pulses such that the one or more target branches of the vagus nerve are activated by the electrical stimulation pulses without causing the contraction of the laryngeal muscle innervated by the RLN.

11. The method of claim 7, comprising:
sensing a stimulation-evoked electroneurographic (ENG) signal representative of a response of the cervical vagus nerve trunk to the electrical stimulation pulses; and
sensing a stimulation-evoked electromyographic (EMG) signal representative of the response of the laryngeal muscle to the electrical stimulation pulses.

12. The method of claim 11, comprising determining one or more stimulation parameters controlling the delivery of the electrical stimulation pulses using the ENG signal and the EMG signal.

13. The method of claim 7, wherein delivering the electrical stimulation pulses to the electrode comprises delivering the electrical stimulation pulses from an implantable medical device to the electrode through an implantable lead coupled between the implantable medical device and the electrode.

14. The method of claim 13, wherein delivering the electrical stimulation pulses to the electrode comprises delivering the electrical stimulation pulses to a cuff electrode configured to be placed on the tVN.

15. The method of claim 13, comprising controlling the delivering the electrical stimulation pulses using one or more stimulation parameters selected for controlling a cardiovascular function.

16. The method of claim 1, further comprising:
sensing a stimulation-evoked electroneurographic (ENG) signal representative of a response of the vagus nerve to the electrical stimulation pulses;
sensing a stimulation-evoked electromyographic (EMG) signal representative of a response of a muscle to the electrical stimulation pulses, the muscle innervated by the second branch of the vagus nerve;
controlling the delivery of the electrical stimulation pulses using a plurality of stimulation parameters; and
adjusting one or more stimulation parameters of the plurality of stimulation parameters using the ENG signal and the EMG signal.

17. The method of claim 16, wherein delivering the electrical stimulation pulses to the electrode placed on or adjacent to the portion of the first branch of the vagus nerve comprises delivering the electrical stimulation pulses to a cuff electrode placed on or adjacent to the portion of the first branch of the vagus nerve.

18. A method for electrically stimulating a vagus nerve in a living body, the method comprising:
delivering electrical stimulation pulses to an electrode placed on a portion of a cervical vagus nerve trunk or a portion of a thoracic vagus nerve (tVN), the portion separate from a second branch of the vagus nerve and selected to allow for substantial activation of one or more target branches of the vagus nerve by the electrical stimulation pulses without substantially activating the second branch;
controlling the delivery of the electrical stimulation pulses such that one or more target branches of the vagus nerve are activated by the electrical stimulation pulses without causing contraction of a laryngeal muscle innervated by a recurrent laryngeal nerve (RLN);
sensing a stimulation-evoked electroneurographic (ENG) signal representative of a response of the cervical vagus nerve trunk to the electrical stimulation pulses;
sensing a stimulation-evoked electromyographic (EMG) signal representative of the response of the laryngeal muscle to the electrical stimulation pulses; and
determining one or more stimulation parameters controlling the delivery of the electrical stimulation pulses using the ENG signal and the EMG signal; and
determining one or more stimulation parameters controlling the delivery of the electrical stimulation pulses to result in an amplitude of the ENG signal exceeding a specified ENG threshold and an amplitude of the EMG signal below a specified EMG threshold.

19. A method for electrically stimulating a vagus nerve in a living body, the method comprising:
delivering electrical stimulation pulses to a cuff electrode placed on or adjacent to a first branch of the vagus nerve, the first branch separate from a second branch of the vagus nerve and selected to allow for substantial activation of one or more target branches of the vagus nerve by the electrical stimulation pulses without substantially activating the second branch;
sensing a stimulation-evoked electroneurographic (ENG) signal representative of a response of the vagus nerve to the electrical stimulation pulses;
sensing a stimulation-evoked electromyographic (EMG) signal representative of a response of a muscle to the electrical stimulation pulses, the muscle innervated by the second branch of the vagus nerve;
controlling the delivery of the electrical stimulation pulses using a plurality of stimulation parameters;
adjusting one or more stimulation parameters of the plurality of stimulation parameters using the ENG signal and the EMG signal; and
storing the one or more stimulation parameters adjusted for an amplitude of the ENG signal exceeding a specified ENG threshold and an amplitude of the EMG signal below a specified EMG threshold.

20. The method of claim 19, wherein controlling the delivery of the electrical stimulation pulses using a plurality of stimulation parameters comprises controlling the delivering the electrical stimulation pulses using one or more stimulation parameters selected for treating an abnormal cardiovascular condition.

* * * * *